United States Patent [19]

Baylin

[11] Patent Number: 5,523,078
[45] Date of Patent: Jun. 4, 1996

[54] METHOD OF PREPARING AND COMPOSITION FOR TREATMENT OF HAIR AND SCALP

[75] Inventor: Michael E. Baylin, 351 South Rd., Pikesville, Md. 21208

[73] Assignee: Michael E. Baylin, Pikesville, Md.

[21] Appl. No.: 383,299

[22] Filed: Feb. 3, 1995

[51] Int. Cl.⁶ ............................................. A61K 7/06
[52] U.S. Cl. ............... 424/70.1; 424/70.4; 424/70.11; 424/70.16; 424/78.02; 514/553; 514/566
[58] Field of Search ................. 424/70.1, 70.4, 424/70.11, 70.16, 78.02; 514/553, 566

[56] References Cited

U.S. PATENT DOCUMENTS

| | | | |
|---|---|---|---|
| 4,170,229 | 10/1979 | Olson | 128/67 |
| 4,728,667 | 3/1988 | Yanagi et al. | 514/458 |
| 4,814,351 | 3/1989 | Mathews et al. | 514/566 |
| 4,847,267 | 7/1989 | Deckner et al. | 514/311 |
| 4,883,659 | 11/1989 | Goodman et al. | 424/78 |
| 4,970,216 | 11/1990 | Deckner et al. | 514/311 |
| 5,011,855 | 4/1991 | Traitler et al. | 514/558 |
| 5,116,607 | 5/1992 | Jones | 424/70 |
| 5,181,529 | 1/1993 | Roberts | 132/209 |
| 5,227,164 | 7/1993 | Lundmark | 424/401 |
| 5,256,477 | 10/1993 | Mahoney | 428/283 |
| 5,270,035 | 12/1993 | Chimento | 424/70 |

*Primary Examiner*—Melvyn I. Marquis
*Assistant Examiner*—Randy Gulakowski
*Attorney, Agent, or Firm*—Leonard Bloom

[57] ABSTRACT

An aqueous composition for the treatment of hair and scalp which includes a chelating agent, gellan gum, a vitamin precursor, a preservative, biotin, a vitamin derivative, γ-linolenic acid, menthol, a liposome, a conditioner, a solubilizer, a conditioner/humectant, folic acid, and a poly amino sugar condensate.

10 Claims, No Drawings

METHOD OF PREPARING AND COMPOSITION FOR TREATMENT OF HAIR AND SCALP

FIELD OF THE INVENTION

The present invention relates to a composition for treatment of hair and scalp. In particular, the present invention includes components which improve hair thickness, hair fullness and overall hair and scalp health.

BACKGROUND ART

Human beings are very conscious of their appearance and especially of the hair on their heads. Over the years, many formulations and treatments have been proposed to treat the hair and the scalp with objectives ranging from the curing of baldness to the cleansing of the hair. Mathews et al in U.S. Pat. No. 4,814,351 disclose a scalp treatment for reduction of hair loss which contains a chelating agent, a surfactant, a conditioner, a vitamin derivative and other ingredients. U.S. Pat. No. 5,116,607 to Jones discloses a hair dressing including petrolatum, a wax, a surfactant, and a hydrolyzed protein. A beautifying hair kit is disclosed in U.S. Pat. No. 5,181,529 issued to Roberts. The kit contains urea, glyoxal and hydrolyzed protein together with other components. Lundmark, in U.S. Pat. No. 5,277,164 discloses a hair treatment composition containing panthenol, allantoin and monohydric alcohol as essential ingredients. In U.S. Pat. No. 5,270,035, Cheminto discloses a hair conditioner containing disodium cocoamphodiacetate, panthenol, polysorbate 80, astringents, nutrients and herb extracts.

Also, various compositions for skin treatment have been disclosed. Goodman et al, in U.S. Pat. No. 4,883,659, discloses a skin treatment preparation which includes a homopolymer, a polyamino sugar condensate, soy protein, amino acids, polysorbate 80, natural oils, panthenol and allantoin acetyl methionine. Taitler et al, in U.S. Pat. No. 5,011,855 discloses a cosmetic and dermatological composition containing γ-linolenic acid obtained from vegetable oils such as borage seed oil. A wound and burn dressing containing gellan gum is disclosed by Mahoney in U.S. Pat. No. 5,256,477.

The composition of the present invention, when used in a regular regimen, include components which improve the overall health of the person's hair and scalp and produce hair which has improved appearance due to the improved hair thickness and hair fullness.

Thus, although some of the components of the present composition have been used for hair treatment and other components have been used for various skin treatments, no one has disclosed a composition which includes the materials of the present invention prepared by the method disclosed herein.

SUMMARY OF THE INVENTION

It is an object of the present invention to provide a composition for treatment of the hair and scalp which improves the health of the hair and the scalp and improves the appearance of the hair by improving the thickness and fullness of the hair.

In accordance with the teachings of the present invention, there is disclosed an aqueous composition for the treatment of hair and scalp comprising a chelating agent, gellan gum, a vitamin precursor, a preservative, biotin, a vitamin derivative, γ-linolenic acid, menthol, a liposome, a conditioner, a solubilizer, a conditioner/humectant, folic acid, a polyamino sugar condensate and diluent ingredients.

DESCRIPTION OF THE PREFERRED EMBODIMENTS

The following is a preferred embodiment of a composition for the treatment of hair and scalp and a method for preparing the composition.

The method involves the combining of ingredients into eight (8) phases and sequentially mixing the ingredients from the phases. The mixing is preferably performed using propeller type agitation. The composition in Table I has been found to be very effective in achieving the objectives of the present invention.

TABLE I

| PHASE | INGREDIENT | CTFA NOMENCLATURE | SUPPLIER | % WT RANGE |
|---|---|---|---|---|
| A | Water | Water | (USP) | 70.00–80.00 |
|  | Hamp-ene Na2 | disodium EDTA | (Grace) | 0.01–0.10 |
|  | KelcoGel F | Gellan gum | (Kelco) | 0.10–1.00 |
| B | Sorbitol-70 | sorbitol | (Dow) | 0.50–3.00 |
|  | dl-Panthenol | panthenol | (Roche) | 0.10–1.50 |
|  | Methylparaben | methylparaben | (USP) | 0.10–0.50 |
|  | Germall 115 | imidazolidinyl urea | (Sutton) | 0.10–0.50 |
|  | Potassium Sorbate | potassium sorbate | (USP) | 0.01–0.50 |
|  | Biotin, USP-FCC | biotin | (Roche) | 0.01–1.00 |
| C | Nicotinate C | tocopherol nicotinate | (BASF) | 0.10–1.50 |
|  | Borage Oil | borage seed oil | (Int'l Flora Tech-602 982–1125) | 0.10–1.00 |
|  | Frescolat | menthyl lactate | (Haarman & Reimer) | 0.50–3.00 |
|  | Exsymol Nanospheres 100 Vitamin E Acetate LPO | tocopherol acetate |  | 0.01–0.50 |
|  | Menthol, USP | menthol | (Barnet) | 0.10–1.00 |

TABLE I-continued

| PHASE | INGREDIENT | CTFA NOMENCLATURE | SUPPLIER | % WT RANGE |
|---|---|---|---|---|
| | Natural Almeth | allantoin acetyl methionine | (ICI) | 0.10–1.00 |
| | Cremophor RH-40 | PEG-40, hydrogenated castor oil | (BASF) | 0.10–5.00 |
| | Sandoxylate SX-424 | PPG-2-Isodeceth-12 | (Sandoz) | 0.10–5.00 |
| | Volpo-10 | oleth-10 | (Croda) | 0.10–3.00 |
| | Tween 80 | polysorbate 80 | (ICI) | 0.10–4.00 |
| D | Water | water | (USP) | 1.00–5.00 |
| E | Merquat Plus 3330 | polyquaternium-39 | (Calgon) | 0.10–3.00 |
| F | Folic Acid, USP | folic acid | (Roche) | 0.01–0.50 |
| | Sodium hydroxide Solution, 10% (to pH 6.5–6.9) | sodium hydroxide | | 0.10–2.00 |
| G | Water | water | (USP) | 2.00–4.00 |
| | Aqualizer EJ | polyamino sugar condensate | (Kolmar) | 0.01–0.25 |
| H | Hydrosoy 2000 SF | hydrolyzed soy protein | (Croda) | 0.01–3.00 |
| | Fragrance #64872-492 | | (Belmay) | 0.01–1.00 |
| TOTAL | | | | 100.00 |

The commercial name and supplier of the components are listed together with the nomenclature of the Cosmetic, Toiletry and Fragrance Association (CTFA). The water must be good quality deionized water since the concentrations of cations (i.e., Ca, Na, K, and Mg) present in normal water will cause the Gellan Gum to gel prematurely and/or form a "hard" gel. Also, the chelating agent (ethylenediaminetetraacetic acid disodium salt) serves as a means of reducing the concentration of cations in addition to acting as an antimicrobiological agent. The Gellan Gel is a thickener. Sorbitol serves as a humectant. Panthenol acts as a moisturizer and is a vitamin B precursor which is helpful in maintaining healthy hair. Methylparaben, imadazolidinyl urea and potassium sorbate all are preservatives. These preservatives may be used individually or in combination with each other. Biotin is a vitamin B member and contributes to healthy hair and scalp. Tocophenyl nicotinate is a vitamin E derivative which stimulates blood flow in the scalp. Borage seed oil is a vegetable oil containing γ-linolenic acid, an essential fatty acid which acts as a therapeutic and nutritional agent. Menthyl lactate provides a cooling sensation to the skin without irritation. Tocopherol acetate is a liposome. Menthol acts as a cooling agent and provides a fragrance to the composition. Allantoin acetyl methionine is a soothing conditioner. The emulsifiers, PEG-40 hydrogenated castor oil and Oleth 10, assist in the formation of the emulsion. PPG-2 Isodeceth-12 is a solublizer to assist in the solvation of the components in water and polysorbate 80 is effective as a sebum solublizer. Polyquaternium-39 is a conditioner/humectant. Folic acid is a B vitamin. The polyamino sugar condensate includes urea which mimics natural moisturizing factors in the skin. Hydrolyzed soy protein is a source of protein and amino acids. Fragrance is added to provide a desired pleasing aroma.

The water of Phase A is heated in a first container to approximately 90° C. and maintained at this temperature for approximately 30 minutes. The water is cooled to approximately 75° C. and is rapidly stirred. The chelating agent is added. The Gellan Gel is slowly sprinkled into the stirring mix. After completion of addition of the Gellan Gum, the components are mixed for 15–20 minutes with high speed agitation. After the Gellan Gel is well dispersed, the components are mixed with medium stirring for approximately 15–20 minutes at 75° C. to deaerate.

The components of Phase A are moderately stirred while the temperature is maintained at 75° C. and the ingredients of Phase B are added in sequence as follows: sorbitol, panthenol, methylparaben, imidazolidinyl urea, potassium sorbate and biotin. The preservatives may be added individually or combined in any manner. The Phase AB mix is moderately stirred for approximately 10–20 minutes, avoiding the incorporation of air.

In a separate, second container, the ingredients of Phase C are combined. These are tocophenyl nicotinate, borage seed oil, menthyl lactate (optional), tocophenyl acetate, menthol, allantoin acetyl methionine, emulsifier such as PEG 40 hydrogenated castor oil and/or Oleth 10 (optional), solublizer such as PPG-2-Isodeceth-1 and/or polysorbate 80 (optional). The ingredients are heated to approximately 70°–75° C. and stirred. The water of Phase D is heated to approximately 75° C. and slowly added to the Phase C components at approximately 75° C. with moderate stirring. After the mixture of Phase CD is homogeneous, the Phase CD mix is added to the first container with Phase AB with moderate stirring and maintaining the temperature at approximately 75° C.

Phase E, polyquaternium-39 is added to the Phase ABCD mix at 75° C. with moderate stirring. The Phase ABCDE is stirred for approximately 10–15 minutes until uniformly mixed.

The Phase ABCDE components are cooled to 60° C. and the folic acid of Phase F is added. The batch turns to an orange-yellow color. The batch is mixed for approximately 15 minutes. A solution of 10% sodium hydroxide is added with moderate stirring to a pH of approximately 6.4 to 7.0. The batch will become white or yellow-white in color. The batch is cooled to approximately 45° C.

The Phase G components (polyamino sugar condensate and water) are combined and added to the Phase ABCDEF batch. The resulting batch is moderately stirred for approximately 15 minutes.

The Phase ABCDEFG components are cooled to approximately 40° C. and the hydrolyzed soy protein and fragrance of Phase H are added in sequence and moderately stirred for about 15 minutes until the entire batch is uniform.

The Phase ABCDEFGH is cooled to room temperature and the pH is adjusted to approximately 6.4 to 7.0 with the sodium hydroxide solution if required. The preferred pH is 6.5. The viscosity is tested and if necessary, 0.2% aqueous sodium chloride solution is added with stirring to obtain a viscosity of approximately 5,000 to 100,000 centipoise (cps). The viscosity has been measured typically, using a Brookfield Viscosimeter, Model LVT, Spindle E at 6 rpm and 18° C. The specific gravity of the composition ranges from approximately 1.000 to 1.020 and the preferred specific gravity is 1.013 g/cc.

The applicant authorized an independent test group to evaluate the composition of the present invention in a double blind study to determine the effects of hair and scalp regimens on hair thickness, hair fullness, and overall hair and scalp health when used according to label instructions. Forty-eight subjects completed the study. At the initiation of the study, visit I, the subjects completed a health questionnaire, an informed consent agreement, an eligibility questionnaire, and a hair and scalp assessment questionnaire. Clinical examinations for hair thickness and hair fullness were conducted. The composition of the present invention was distributed to 26 subjects and a placebo which was visually similar but which contained no active ingredients, was distributed to 22 subjects. All of the subjects were instructed both verbally and in writing how to use the product. The subjects returned for visit II following approximately one week of usage and completed a second hair and scalp assessment questionnaire as well as a final questionnaire. Clinical examinations for hair thickness and hair fullness were again conducted. Clinical examinations revealed statistically significant increases ($p \leq 0.05$) in hair thickness and hair fullness from visit I to visit II in the active group. No statistically significant increases were observed, however, in hair thickness and hair fullness from visit I to visit II in the placebo group. Analysis of the visit II hair and scalp assessment questionnaire revealed that 46–62% of the subjects in the active group had self-perceived improvements in hair thickness, hair fullness, and hair and scalp health. Of the subjects in the placebo group, 41–50% had self-perceived improvements in hair thickness, hair fullness, and hair and scalp health.

A second study was conducted by the independent test group using twelve subjects. At visit I, subjects completed a health questionnaire, an informed consent agreement, an eligibility questionnaire, and a hair and scalp questionnaire. Clinical examinations for hair thickness and hair fullness were conducted, and three subjects with self-perceived hair damage had approximately ten hairs plucked from the area of damage. These hairs were examined for split ends and cuticle damage using a Zeiss Derma Vision® Stereomicroscope/Video System. The composition of the present invention was distributed to the subjects, and the subjects were instructed both verbally and in writing how to use the product. Subjects returned for visit II following one week of usage and completed a second hair and scalp questionnaire as well as a final questionnaire. Clinical examinations for hair thickness and hair fullness were again conducted, and the three subjects with self-perceived hair damage at visit I again had approximately ten hairs plucked from the area of damage. Analysis of damaged hair samples showed examples of repair in split ends and cuticle damage from visit I to visit II. However, because of the small hair fiber sample size, no conclusion can be drawn about the effect of the test material on hair damage repair. Clinical examinations revealed statistically significant increases ($p \leq 0.05$) in hair thickness and hair fullness from visit I to visit II. Furthermore, analysis of the visit II hair and scalp questionnaire revealed that 75%–83% of the subjects had self-perceived moderate or large improvements in hair thickness and hair fullness.

Obviously, many modifications may be made without departing from the basic spirit of the present invention. Accordingly, it will be appreciated by those skilled in the art that within the scope of the appended claims, the invention may be practiced other than has been specifically described herein.

What is claimed is:

1. An aqueous composition for the treatment of hair and scalp comprising: ethylenediaminetetraacetic acid disodium salt, gellan gum, dl-panthenol, a preservative, biotin, tocopherol nicotinate γ-linolenic acid, menthol, tocopherol acetate, allantoin acetyl methionine, a solubilizer, polyquaternium-39, folic acid, a polyamino sugar condensate and diluent ingredients, wherein the percent by weight are in the ranges of: water 73%–89%, ethylenediaminetetraacetic acid disodium salt 0.01%–0.1%, gellan gum 0.1%–1%, dl-panthenol 0.1%– 1.5% preservative 0.2%–15% biotin 0.01%–1%, tocopherol nicotinate 0.1%–1.5%, γlinolenic acid 0.1%–1%, menthol 0.1%–1%, tocopheral acetate 0.01%–5%, allantoin acetyl methionine 0.1%–1%, solubilizer 0.1%–4%, polyquaternium-39 0.1%–3% polyamino sugar condensate 0.1%–0.25% and diluent ingredients to add to 100%.

2. The composition of claim 1, wherein the preservative is selected from the group consisting of methyl paraben, imidazolidinyl urea, potassium sorbate and mixtures thereof.

3. The composition of claim 1, wherein the solublizer is selected from the group consisting of PPG-2-isodeceth-12, polysorbate 80 and mixtures thereof.

4. The composition of claim 1, wherein the polyamino sugar condensate is blended with urea.

5. The composition of claim 1, wherein the pH is approximately 6.4 to 7.0.

6. The method of preparing an aqueous composition for the treatment of hair and scalp comprising the steps of:

heating deionized water 70%–80% in a first container to approximately 90° C. for approximately 30 min., cooling to approximately 75° C. and adding ethylenediaminetetraacetic acid disodium salt 0.01%–0.1%, stirring rapidly while slowly adding gellan gum 0.1%–1%, mixing with moderate stirring for approximately 15–20 min. at 75° C.;

with moderate stirring at 75° C., adding sequentially dl-panthenol 0.1%–1.5%, a preservative 0.2%– 1.5% and biotin 0.01%–1% and continuing stirring for approximately 10–20 min., avoiding the incorporation of air into the solution;

in a separate second container, placing tocopherol nicotinate 0.1%–1.5%, γ-linolenic acid 0.1%–1% menthol 0.1%–1%, tocopheral acetate 0.01%–0.5%, allantoin acetyl methionine 0.1%–1%, a solubilizer 0.1%–5% and diluent ingredients 0.8%–15%, heating to approximately 70° C.–75° C. with stirring, slowly adding deionized water 0.1%–5% heated to approximately 75° C. while stirring moderately until homogeneous;

adding the components from the second container to the first container with moderate stirring while maintaining the temperature at approximately 75° C.;

adding polyquaternium-39 0.1%–3% to the first container at approximately 75° C. with moderate stirring and mixing for approximately 10–15 min.;

cooling the contents of the first container to approximately 60° C., adding folic acid 0.1%–0.5% and stirring for approximately 15 min., adjusting to a pH of approximately 6.4 to 7.0 and cooling to approximately 45° C.;

mixing a polyamino sugar condensate 0.1%–0.25% with distilled water 2%–4% and adding the mix to the contents in the first container and stirring moderately for approximately 15 minutes;

cooling the contents of the first container to approximately 40° C. and adding, in sequence with moderate stirring, a hydrolyzed protein 0.1%–3% and a fragrance 0.01%–1%, stirring with moderate agitation for approximately 15 minutes; wherein all the ranges are percent by weight and cooling to room temperature and adjusting to a pH of approximately 6.4 to 7.0.

7. The method of claim 6, wherein the preservative is selected from the group consisting of methylparaben, imidazolidinyl urea, potassium sorbate and mixtures thereof.

8. The method of claim 6, wherein the solubilizer is selected from the group consisting of PPG-2-isodeceth-12, polysorbate 80 and mixtures thereof.

9. The method of claim 6, wherein the polyamino sugar condensate is blended with urea.

10. The method of claim 6, wherein the viscosity of the composition ranges from 5,000 to 100,000 centipoise.

* * * * *

UNITED STATES PATENT AND TRADEMARK OFFICE
CERTIFICATE OF CORRECTION

PATENT NO. : 5,523,078
DATED : June 4, 1996
INVENTOR(S) : Baylin

It is certified that error appears in the above-indentified patent and that said Letters Patent is hereby corrected as shown below:

Column 6, line 34, after "1.5% " and before "preservative", insert therein -- , -- .

Column 6, line 35 change "15%" to read -- 1.5% -- .

Column 6, line 36, change "ϒlinolenic acid" to read -- ϒ-linolenic acid -- .

Signed and Sealed this

Twenty-seventh Day of August, 1996

Attest:

BRUCE LEHMAN

Attesting Officer     Commissioner of Patents and Trademarks